United States Patent [19]
Rothenberg et al.

[11] Patent Number: 6,073,818
[45] Date of Patent: Jun. 13, 2000

[54] APPARATUS FOR CONTROLLED DELIVERY OF POWDERED SOLID MATERIALS

[75] Inventors: Simon J. Rothenberg, North Wales; Richard Joel Hershman, Croydan, both of Pa.; Brian Alan Wong, Cary, N.C.

[73] Assignee: Genzyme Transgenics Corporation, Framingham, Mass.

[21] Appl. No.: 09/099,979

[22] Filed: Jun. 19, 1998

[51] Int. Cl.[7] .................................................. B65D 83/00
[52] U.S. Cl. ........................ 222/637; 222/412; 222/413; 222/630; 406/61
[58] Field of Search .................................... 222/333, 334, 222/410, 412, 413, 630, 637; 406/61, 151–153

[56] References Cited

U.S. PATENT DOCUMENTS

| | | | |
|---|---|---|---|
| 4,409,009 | 10/1983 | Lissy | 55/302 |
| 4,502,820 | 3/1985 | Fujii et al. | 222/413 |
| 4,619,380 | 10/1986 | Brooks | 222/413 |
| 5,240,185 | 8/1993 | Kaiju et al. | 222/412 |
| 5,409,139 | 4/1995 | Daussan et al. | 222/413 |
| 5,419,987 | 5/1995 | Goldstein et al. | 429/229 |
| 5,524,796 | 6/1996 | Hyer | 222/413 |
| 5,634,713 | 6/1997 | Abe | 406/61 |
| 5,702,209 | 12/1997 | Mauchle | 406/153 |
| 5,713,494 | 2/1998 | Kaiju et al. | 222/637 |

*Primary Examiner*—J. Casimer Jacyna
*Attorney, Agent, or Firm*—Woodcock Washburn Kurtz Mackiewicz & Norris LLP

[57] ABSTRACT

Apparatus and methods for accurate delivery of relatively small quantities of powdered solid materials. Preferred apparatus comprise: a primary chamber having a lateral surface extending between a first open end and a second open end; a rotating member that is positioned within the primary chamber and extends from a first position within the primary chamber to a second position within the primary chamber; a motor coupled with the rotating member and adapted to effect rotation thereof; a feed chamber having a lateral surface extending between a first open end and a second open end; and an air flow chamber coupled with the primary chamber and having a lateral surface extending between a first open end and a second open end.

32 Claims, 1 Drawing Sheet

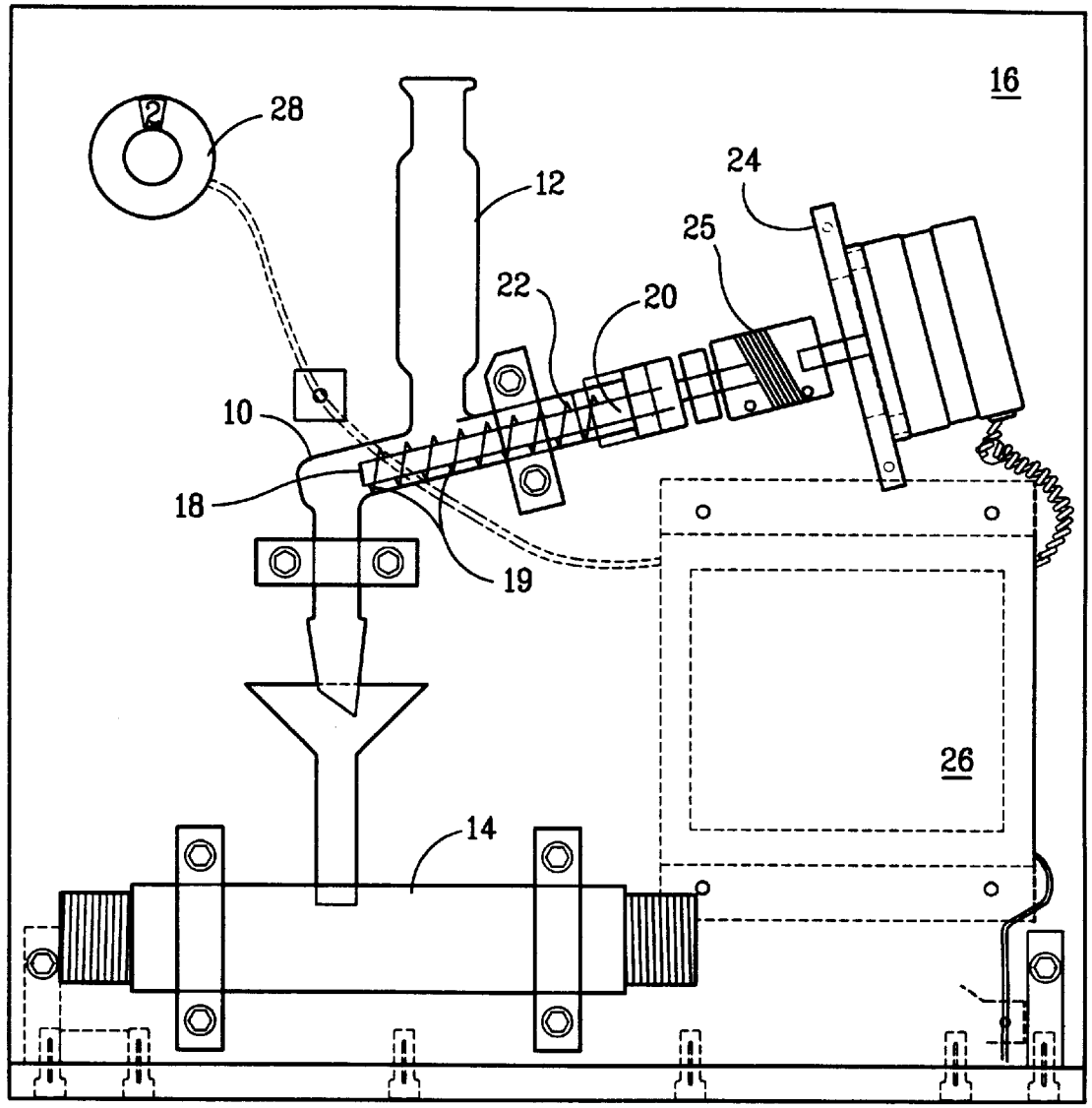

APPARATUS FOR CONTROLLED DELIVERY OF POWDERED SOLID MATERIALS

FIELD OF THE INVENTION

The present invention is directed to apparatus for delivering solid materials such as finely divided powders and, more particularly, to apparatus for delivering carefully-metered, relatively small quantities of such materials.

BACKGROUND OF THE INVENTION

Dry powder inhalers have been increasingly used for the delivery of pharmaceuticals to the respiratory tract. In toxicity studies with such materials, one typically adjusts the duration of exposure and aerosol concentration to ensure that test animals receive doses that are appropriate in view of the dosages that one intends to use in subsequent clinical studies.

Most pharmaceuticals that undergo toxicity testing are quite expensive as they are produced on laboratory-scale equipment using procedures that have not yet been optimized. Due to this expense, toxicity testing of new pharmaceuticals typically employs as small a quantity of the pharmaceutical as possible. Thus, there has been a trend away from whole-body animal exposure chambers, which employ relatively large quantities of the test pharmaceutical, to more efficient, second generation devices such as, for example, nose-only chambers. Many of the dry powder aerosol generators that are available, however, have been designed for use with the whole-body exposure chambers and cannot reliably achieve the significantly lower throughput rates of solid material required for the second generation devices.

Consequently, there is a need in the art for devices that can reliably and accurately provide relatively small amounts of solid material for eventual entrainment in an air stream.

BRIEF DESCRIPTION OF THE INVENTION

The present invention provides apparatus and methods for the delivery of small amounts of powdered solid materials and for the generation of dry powder aerosols from such materials.

In preferred embodiments, the apparatus of the invention comprise a primary chamber having a lateral surface extending between a first open end and a second open end and a rotating member positioned within the primary chamber and extending from a first position within the primary chamber to a second position within the primary chamber. The rotating member is coupled with a motor adapted to effect rotation. The apparatus of the invention further comprise a feed chamber (or reservoir) having a lateral surface extending between a first open end and a second open end. The first end of the feed chamber not only is coupled with the primary chamber through the primary chamber's lateral surface at a point between the first and second positions, but also is adapted to both receive a solid material through its second end and transfer the solid material (preferably through the force of gravity) into the primary chamber. The apparatus of the invention also comprise an air flow chamber having a lateral surface extending between a first open end and a second open end. The air flow chamber is coupled with one end of the primary chamber through the air flow chamber's lateral surface and is adapted to receive the solid material from the primary chamber.

The present invention further provides processes for delivering powdered solid material. Preferred processes comprise the steps of placing a powdered solid material into the feed chamber and actuating the motor to effect delivery of the solid material to the air flow chamber.

BRIEF DESCRIPTION OF THE DRAWINGS

The numerous objects and advantages of the present invention may be better understood by those skilled in the art by reference to the accompanying non-scale figure, in which:

FIG. 1 s an elevation view of an apparatus the invention.

DETAILED DESCRIPTION OF THE INVENTION

The present invention provides apparatus and processes for delivering solid materials. Solid materials according to the invention can be in pure form or can themselves be mixtures of different materials, although they should be in a sufficiently finely divided state and/or of sufficiently low density that they remain in an air stream over a suitable distance of interest. Preferred solid materials are those having particle size less than about 10 $\mu$m diameter, with those having particle size between about 1 and about 6 $\mu$m diameter being particularly preferred.

The apparatus of the invention include a primary chamber having a lateral surface extending between a first open end and a second open end. In general, the primary chamber should present lateral cross-sections of relatively constant size along its length, particularly in that portion of the primary chamber in which the rotating member is positioned. Cylindrical chambers (i.e., those having circular cross-section) are preferred. It is also preferred that the primary chamber be substantially L-shaped as one proceeds from its first end to its second end. In preferred embodiments the first and second ends form an angle of about 90° to about 135°. The primary chamber need not have any particular dimensions, although it is believed that the chamber should have a length of about 5 to 20 centimeters and a diameter of about 1 to 6 centimeters. The chamber can be constructed from a wide variety of materials such as glass, metal, or plastic, although transparent materials are preferred.

The apparatus of the invention include a feed chamber coupled with the primary chamber and adapted to effect transfer of a powdered solid material to the primary chamber. The feed chamber also has a lateral surface extending between a first open end and a second open end, with the first end of the feed chamber preferably being directly attached to the primary chamber through an aperture in the primary chamber's lateral surface. The chambers preferably meet to form an angle of about 45° to about 90°. The feed chamber also need not have any particular dimensions, although it is believed that the chamber should have a height of about 2 to 20 centimeters and a diameter of about 2 to 5 centimeters. The chamber can be constructed from a wide variety of materials such as glass, metal, or plastic, with transparent materials being preferred. In preferred embodiments, the second end of the feed chamber (i.e., the end through which the solid material enters) is coupled with a source of flowing (preferably dry) air that can pass over the solid material during its residence in the feed chamber.

As noted, primary chambers according to the invention include a rotating member, the general purpose of which is to effect, through its rotation, a controlled transfer of the solid material from the feed chamber, through at least a portion of the primary chamber, to the air flow chamber. Representative rotating members include screws and rigid rods around which one or more flexible, substantially cylindrical filaments are coiled. Preferred rotating members are those, such as screws, that comprise at least two vanes defining a volume therebetween. The term vane, as used herein, refers to the raised, somewhat helical portion of a screw that is encountered (upon one complete rotation of the screw) by an object that is fixed at a position facing the screw and transverse thereto. The term vane also refers to corresponding structures such as, for example, those produced by wrapping a flexible filament helically around a rod. The volume defined by two adjacent vanes preferably is about 0.05 to about 1 cm$^3$, i.e., one complete rotation of the rotating member preferably results in the transfer of such a volume of solid material along the rotating member's length. The number of vanes presented by the rotating member can be fixed (as with a screw) or variable (as with a filament wrapped around a rod). In preferred embodiments, the rotating member is about 15 centimeters long and about 1 to 5 centimeters wide, and comprises about 2 vanes per centimeter along its length. Preferred assemblies comprising a feed chamber, a primary chamber, and a rotating member include the model D102389 or D102702 solids addition funnels that are commercially available from Ace Glass Company, Vineland, N.J.

Rotation of the rotating member is effected in accordance with the invention through actuation of a motor coupled therewith. A motor according to the invention is any electromechanical device that is capable of delivering sufficient force to rotate the rotating member. Preferred motors are those which deliver such force in a discontinuous manner only at set intervals such that there are alternating periods of time during which the motor is active and quiescent. Preferably, the motor delivers the necessary force to the rotating member in short, angular pulses of about 0.5° to 5° rotation per pulse for a duration of about 0.1 to about 1 millisecond per pulse at a rate of about 0.3 to 30 pulses per second to achieve about 0.05 to about 20 revolutions per minute (rpm), preferably about 0.1 to about 10 rpm. Particularly preferred are motors are those that are coupled with so-called "stepper" drives. One preferred motor is the model SPH-54AB-094 motor (Tokyo Electric Co, Tokyo, Japan) coupled with the model TM93KIT2421 stepper drive (Herbach & Rademan, Mount Laurel, N.J.).

Rotation of the rotating member ideally facilitates (together with gravity) the passage of the powdered solid material through the primary chamber to the air flow chamber at a rate of from about 0.02 to about 200 cm$^3$ per hour (i.e., about 0.01 to about 100 grams per hour for most materials), more preferably at a rate of from about 0.2 to about 20 cm$^3$ per hour (about 0.1 to about 10 grams per hour). This is, of course, dependent upon the number and spacing of the vanes. In general, one increases the throughput of solid material per rotation by reducing the number of vanes per unit length of the rotating member or by reducing the screw diameter and the rate of rotation.

Air flow chambers according to the invention are generally tubular with a lateral surface extending between first and second open ends. The air flow chamber is coupled with the primary chamber, preferably through the an aperture, coupling, or adapter in the air flow chamber's lateral side. In preferred embodiments, one end of the primary chamber is positioned over an aperture in the air flow chamber's lateral side and a reducing adapter such as a funnel is placed in the aperture to receive the solid material. The air flow chamber need not have any particular dimensions, although it preferably has a length of about 20 to 100 centimeters and a width of about 1 to 5 centimeters. The chamber can be constructed from a wide variety of materials such as glass, metal, or plastic, with metals being preferred. Particularly preferred air flow chambers are the Venturi Jet devices that are commercially available from IN-TOX® (Albuquerque, N. Mex.).

In preferred embodiments of the invention, the air flow chamber is coupled at its first end with a pump, fan, tank or some other source of air at a pressure that is greater than atmospheric pressure, usually above 10 psi. Coupling of the air chamber and air source in this manner allows the air to pass substantially along an axis defined by the chamber's first and second ends and thereby entrain solid material which enters the chamber's lateral side. The Venturi jet causes suction of air and powder through the aperture in the air flow chamber's lateral side. The air should pass through the air flow chamber at a rate of about 5 to about 80 liters per minute, preferably at a rate of about 20 to about 70 liters per minute. The rate at which air passes through the air flow chamber and the rate at which solid material enters the air flow chamber preferably are adjusted to ensure that the solid material is entrained in the flowing air at a concentration of about 0.1 to about 1000 micrograms per liter, more preferably at a concentration of about 1 to about 500 micrograms per liter. In such embodiments, it is preferred that the apparatus of the invention further comprise a receptacle that is coupled with the second end of the air flow chamber and is adapted to receive the flowing air and the solid material entrained therein. The receptacle need not have any particular shape, and preferably is a tube or pipe that, in turn, is coupled with an animal exposure chamber.

One preferred apparatus according to the invention is shown in FIG. 1, in which primary chamber 10, feed chamber 12, and air flow chamber 14 are mounted on panel 16. Contained within primary chamber 10 is rotating member 18 comprising rod 20 and coiled filament 22. Rotation of rotating member 18 is effected using motor 24 via coupling 25. Motor 24, in turn, is coupled with stepper drive 26 which, in turn, is coupled with speed control 28. Upon rotation of member 18, vanes 19 proceed along a portion of primary chamber 10 and, in the process, move solid material (not shown) entering from feed chamber 12 to air flow chamber 14, where the powdered solid material is entrained in flowing air provided by an air source (not shown).

The device shown in FIG. 1 typically is operated by rotating member 18 at about 0.1 to 10 rpm to provide solid material throughput rates of about 1 to 20 cm$^3$ per hour (about 0.5 to 10 grams per hour). In instances in which solid material clumps or otherwise jams rotation of member 18, primary chamber 10 preferably is shaken manually or with an electromechanical vibrator. With the typical throughput rates, and air flow rates of about 20 to 70 liters per minute, the device generally can achieve a solid material concentration of 10 to 1000 micrograms per liter entrained in the air exiting air flow chamber 14.

Additional objects, advantages, and novel features of this invention will become apparent to those skilled in the art upon examination of the following examples thereof, which are not intended to be limiting.

EXAMPLE 1

The feed chamber of an apparatus such as shown in FIG. 1 was filled with moist α-lactose, and no precautions taken to exclude moisture. This material rapidly formed an arch at the bottom of the feed chamber, and clumps of α-lactose powder were formed in both the primary chamber and the funnel inlet to the air flow chamber. No continuous runs longer than 15 minutes were achieved with moist α-lactose.

When dry α-lactose, which flowed freely, was placed in the feed chamber, and dry air bled into that chamber, the system ran smoothly for longer periods of time. In the course of twenty 60-minute test runs, generating aerosols ranging from 10 µg/L to 500 µg/L, the system had to be cleared only once or twice per run.

The flow of high pressure air into the air flow chamber generator is accompanied by a flow of air sucked into the funnel. This airflow assists the transport of powder into the funnel and was found to be linearly related to the inlet flow to the air flow chamber.

Aerosol concentrations ranging from 20 µg/L to 500 µg/L, corresponding to rotation speeds ranging from 0.125 to 9 rpm were generated by varying the potentiometer setting on the rotating member over the available range of settings. Lower speeds were achieved by using a half-speed circuit within the stepper drive. Test article concentrations were found to be quite stable. Test article consumption ranged from 0.2 to 5 g/hr, and delivery efficiencies ranged form 20 to 30%. Lower test article concentrations (5 µg/L to 10 µg/L) were successfully obtained by reducing the inlet flow into the air flow chamber from 40 to 30 or 20 LPM, and adding dilution air at the top of the one inch delivery line to a downstream exposure chamber to give a total flow of 40 LPM. Alternatively, very low concentrations are attained by using a push-pull diluter system, as described in AAAR abstract #5PR4, 1997.

The particle size range generated (mass median aerodynamic diameter (MMAD, in µm) of 1.8 to 2.4 µm) was respirable. At the flow rates used, 30 to 45 LPM, the horizontal and vertical one inch lines leading to the animal exposure chamber acted as effective elutriators. A few aggregates of particles were seen dropping out of the screw feeder into the funnel of the air flow chamber. The majority of these aggregates were dispersed in the air flow chamber, but some were found deposited in the lines delivering aerosol to the chamber. Thus the aerosol delivered to the chamber was a respirable aerosol, as required for inhalation studies.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An apparatus comprising:
    a primary chamber having a lateral surface extending between a first open end and a second open end;
    a rotating member positioned within said primary chamber and extending from a first position within said primary chamber to a second position within said primary chamber;
    a motor coupled with said rotating member and adapted to effect rotation thereof at a rate of about 0.1 to about 10 rpm;
    a feed chamber having a lateral surface extending between a first open end and a second open end, said first end of said feed chamber being coupled with said primary chamber through said lateral surface of said primary chamber at a point between said first position and said second position, said feed chamber being adapted to receive a powdered solid material through said second end thereof and transfer said solid material into said primary chamber;
    an air flow chamber having a lateral surface extending between a first open end and a second open end, said air flow chamber being coupled with one end of said primary chamber through said lateral surface of said air flow chamber and being adapted to receive said solid material from said primary chambers;
    wherein actuation of said motor is selected from the group consisting of:
        said motor effecting rotation of said rotating member at fixed intervals; or
        said motor applying pulses of force to said rotating member at a rate of about 0.3 to about 30 pulses per second.

2. The apparatus of claim 1 wherein said lateral surface of said primary chamber has a substantially circular cross-section between said first position and said second position.

3. The apparatus of claim 1 wherein said first and second ends of said primary chamber form an angle of from about 90° to about 135°.

4. The apparatus of claim 1 wherein said rotating member is about 15 centimeters long.

5. The apparatus of claim 1 wherein said rotating member comprises at least two vanes defining a volume therebetween.

6. The apparatus of claim 5 wherein said volume is about 0.05 to about 1 cm$^3$.

7. The apparatus of claim 1 wherein said rotating member comprises about 2 vanes per centimeter along its length.

8. The apparatus of claim 1 wherein said rotating member comprises a screw.

9. The apparatus of claim 1 wherein said rotating member comprises a filament coiled around a rod.

10. The apparatus of claim 1 wherein said feed chamber and said primary chamber meet to form an angle of from about 45° to about 90°.

11. The apparatus of claim 1 wherein said primary chamber and said air flow chamber are coupled through a reducing adapter.

12. The apparatus of claim 11 wherein said reducing adapter is a funnel extending into said air flow chamber.

13. The apparatus of claim 1 further comprising said solid material.

14. The apparatus of claim 13 wherein said solid material has particle size less than about 10 µm.

15. The apparatus of claim 13 wherein said solid material has particle size between about 1 and about 6 µm.

16. The apparatus of claim 1 further comprising air flow means coupled with said second end of said feed chamber.

17. The apparatus of claim 1 further comprising a source of air at a pressure that is greater than atmospheric pressure, said source of air being coupled with said first end of said air flow chamber and adapted for passing said air substantially along an axis defined by said first and second ends of said air flow chamber.

18. The apparatus of claim 17 wherein said solid material is entrained in said air at a concentration of about 0.0 to about 1000 micrograms per liter.

19. The apparatus of claim 1 further comprising a receptacle coupled with said second end of said air flow chamber and adapted to receive said air and said solid material.

20. A process for delivering powdered solid material comprising the steps of:
    providing an apparatus comprising:
        a primary chamber having a lateral surface extending between a first open end and a second open end;
        a rotating member positioned within said primary chamber and extending from a first position within said primary chamber to a second position within said primary chamber;

a motor coupled with said rotating member and adapted to effect rotation thereof at a rate of about 0.1 to about 10 rpm;

a feed chamber having a lateral surface extending between a first open end and a second open end, said first end of said feed chamber being coupled with said primary chamber through said lateral surface of said primary chamber at a point between said first position and said second position, said feed chamber being adapted to receive a powdered solid material through said second end thereof and transfer said solid material into said primary chamber;

an air flow chamber having a lateral surface extending between a first open end and a second open end, said air flow chamber being coupled with one end of said primary chamber through said lateral surface of said air flow chamber and being adapted to receive said solid material from said primary chamber;

placing said solid material into said feed chamber; and actuating said motor to effect delivery of said solid material to said air flow chamber;

wherein actuation of said motor is selected from the group consisting of:

said motor effecting rotation of said rotating member at fixed intervals; or said motor applying pulses of force to said rotating member at a rate of about 0.3 to about 30 pulses per second.

21. The process of claim 20 wherein said motor effects rotation of said rotating member at from about 0.05 to about 20 rpm.

22. The process of claim 20 wherein said motor effects rotation of said rotating member at from about 0.1 to about 10 rpm.

23. The process of claim 20 wherein said motor effects rotation of said rotating member at fixed intervals.

24. The process of claim 20 wherein said motor applies pulses of force to said rotating member at a rate of about 0.3 to about 30 pulses per second.

25. The process of claim 24 wherein each of said pulses effect about 0.5° to about 5° rotation of said rotating member.

26. The process of claim 20 wherein said solid material is delivered to said air flow chamber at a rate of from about 0.02 to about 200 $cm^3$ per hour.

27. The process of claim 20 wherein said solid material is delivered to said air flow chamber at a rate of from about 0.2 to about 20 $cm^3$ per hour.

28. The process of claim 20 further comprising passing air through said air flow chamber.

29. The process of claim 28 wherein said air passes through said air flow chamber at a rate of about 5 to about 80 liters per minute.

30. The process of claim 28 wherein said air passes through said air flow chamber at a rate of about 20 to about 70 liters per minute.

31. The process of claim 28 wherein said solid material is entrained in said air at a concentration of about 0.1 to about 1000 micrograms per liter.

32. The process of claim 28 wherein said solid material is entrained in said air at a concentration of about 1 to about 500 micrograms per liter.

* * * * *